United States Patent [19]

Perregaard

[11] Patent Number: 4,710,500
[45] Date of Patent: Dec. 1, 1987

[54] 1-(4'-FLUOROPHENYL)-3,5-SUBSTITUTED INDOLES USEFUL IN THE TREATMENT OF PSYCHIC DISORDERS AND PHARMACEUTICAL COMPOSITIONS THEREOF

[75] Inventor: Jens K. Perregaard, Oelstykke, Denmark

[73] Assignee: H. Lundbeck A/S, Copenhagen-Valby, Denmark

[21] Appl. No.: 846,912

[22] Filed: Apr. 1, 1986

[30] Foreign Application Priority Data

Apr. 10, 1985 [GB] United Kingdom ............... 8509164

[51] Int. Cl.$^4$ .................. A61K 31/495; C07D 403/14; C07D 403/04; C07D 401/04
[52] U.S. Cl. .................................. 514/254; 514/339; 514/253; 544/54; 544/55; 544/96; 544/97; 544/295; 544/364; 544/369; 544/370; 544/371; 544/373; 546/256; 546/257; 546/273
[58] Field of Search ............... 544/364, 373, 374, 54, 544/55, 96, 97, 295, 369, 370, 371; 514/252, 254, 339, 253; 546/256, 257, 273

[56] References Cited

U.S. PATENT DOCUMENTS 3,429,886  2/1969  Beck ................................. 544/373

FOREIGN PATENT DOCUMENTS 22705    1/1981  European Pat. Off. .
2811031  9/1978  Fed. Rep. of Germany .

OTHER PUBLICATIONS

Guillaume et al., CA 94-156767g.
Buzas et al., CA 90-38962m.
Buzas et al., CA 93-8014y.

Primary Examiner—Donald G. Daus
Assistant Examiner—Cecilia Shen
Attorney, Agent, or Firm—Gordon W. Hueschen

[57] ABSTRACT

The present invention relates to novel indole derivatives which have interesting pharmacodynamic effects indicating pronounced activity in the treatment of psychic disorders, especially psychoses and, at the same time, a low degree of undesired side effects.

Moreover, the invention relates to methods for the preparation of said indole derivatives, pharmaceutical compositions containing same, and methods for the treatment of psychic disorders, especially psychoses, by administering a therapeutically active amount of one of said derivatives to a living animal body, including human beings.

The novel indole derivatives of the present invention are represented by the following formula:

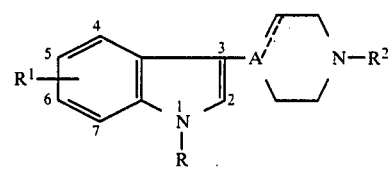

wherein R is phenyl, optionally substituted with halogen, lower alkyl or trifluoromethyl, or a hetero aromatic group, such as 2-thienyl, 3-thienyl, 2-furoyl, 3-furoyl, 2-thiazol, 2-oxazol, 2-imidazole, 2-pyridyl, 3-pyridyl or 4-pyridyl; $R^1$ is hydrogen, halogen, lower alkyl, lower alkoxy, hydroxy, cyano, nitro, lower alkylthio, trifluoromethyl, lower alkylsulfonyl, amino, lower alkylamino or lower di-alkylamino; "A" is nitrogen or carbon, and the dotted line indicates—when A is carbon—an optional bond; $R^2$ is hydrogen, cycloalkyl, lower alkyl or lower alkenyl, optionally substituted with one or two hydroxy groups, any hydroxy group present being optionally esterified with an aliphatic carboxylic acid radical having from two to twenty-four carbon atoms inclusive, or $R^2$ is the group

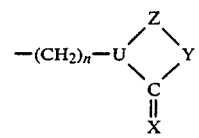

wherein "n" is an integer of 2-6; X is oxygen or sulfur, or >C=X may constitute the group >CH= when Y is =N— or =CH—; Y is oxygen, sulfur, $CH_2$ or N $R^3$, where $R^3$ is hydrogen or lower alkyl, lower alkenyl or a cycloalkylmethyl group, said "cycloalkyl" having from three to six carbon atoms inclusive; Z is —($CH_2)_m$—, "m" being 2 or 3, or Z is —CH=CH— or 1,2-phenylene optionally substituted with halogen or trifluoromethyl, or Z is —CO(or S)$CH_2$—; U is nitrogen or carbon, provided that when $R^1$ is chloro, A is nitrogen and $R^2$ is methyl or cyclohexyl, R may not be phenyl; as well as their pharmaceutically acceptable acid addition salts.

9 Claims, No Drawings

1-(4'-FLUOROPHENYL)-3,5-SUBSTITUTED INDOLES USEFUL IN THE TREATMENT OF PSYCHIC DISORDERS AND PHARMACEUTICAL COMPOSITIONS THEREOF

BACKGROUND OF THE INVENTION

In the past, several indole derivatives being substituted at the nitrogen atom with a carboxylic acid radical have been found to possess analgetic and antiinflammatory properties. Recently it was suggested in German OLS No. 2811031 that also indoles having a phenylsubstituent at the nitrogen atom might have the desired analgetic or antiinflammatory effects, but no data were given for the 1-phenyl-5-chloro-3-methylpiperanzine-indole or 1-phenyl-5-chloro-3-cyclohexyl-piperazine-indole actually disclosed in the specification. We have prepared the first-mentioned of these compounds (Lu 23-015) and found that it was without interesting effects in the pharmacological testing carried out in our laboratories.

In European Patent Application No. 80401005.6 some derivatives of tetrahydro-pyridinyl-indoles having at the 1-position either hydrogen or alkyl (1-3 C-atoms), were described as being neuroleptics. The pharmacological data given in the specification, however, indicate only weak to moderate neuroleptic activity.

We have prepared one of these compounds, 5-chloro-3-(1-(2-hydroxyethyl)-1,2,3,6-tetrahydropyrid-4-yl)indol (Lu 23-143) and found that it was almost inactive compared with the compounds of Formula I.

It has now surprisingly been found that the novel indole derivatives of Formula I are potent dopaminergic antagonists in pharmacological tests, both in vivo and in vitro, as compared with wellknown neuroleptics commonly used in the treatment of psychoses; and especially very long-lasting effects - up to several days - were observed with many of the compounds of Formula I. Additionally, most of the the indoles of Formula I are strong 5-HT antagonists both periferically and centrally, which is considered to be important for the treatment of psychic disorders or cardiovascular diseases.

The terms lower alkyl, lower alkoxy, lower alkylthio and lower alkysulfonyl designate such groups having from one to four carbon atoms inclusive. Exemplary of such groups are methyl, ethyl, n-propyl, iso-propyl, n-butyl, sec.butyl, methoxy, ethoxy, propoxy, butoxy, methylthio, ethylthio, propylthio, methylsulfonyl, ethylsulfonyl, or the like.

The term lower alkenyl designates alkenyl groups having from two to four carbon atoms, for example ethenyl, 1-propenyl, 2-butenyl, or the like.

This invention also includes pharmaceutically acceptable salts of the compounds of Formula I formed with non-toxic acids. Such salts are easily prepared by methods known to the art.

The base is reacted with either the calculated amount of organic or inorganic acid in an aqueous miscible solvent, such as acetone or ethanol, with isolation of the salt by concentration and cooling or an excess of the acid in aqueous immiscbile solvent, such as ethyl ether or chloroform, with the desired salt separating directly.

Exemplary of such organic salts are those with maleic, fumaric, benzoic, ascorbic, embonic, succinic, oxalic, bis-methylenesalicylic, methanesulfonic, ethanedisulfonic, acetic, propionic, tartaric, salicylic, citric, gluconic, lactic, malic, mandelic, cinnamic, citraconic, aspartic, stearic, palmitic, itaconic, glycolic, p-aminobenzoic, glutamic, benzene sulfonic and theophylline acetic acids, as well as the 8-halotheophyllines, for example 8-bromo-theophylline. Exemplary of such inorganic salts are those with hydrochloric, hydrobromic, sulfuric, sulfamic, phosphoric and nitric acids. Of course, these salts may also be prepared by the classical method of double decomposition of appropriate salts, which is wellknown to the art.

The compounds of Formula I as well as the pharmaceutically acceptable acid addition salts thereof may be administered both orally and parenterally, for example in the form of tablets, capsules, powders, syrups or solutions for injection.

Of the indoles of Formula I, those wherein $R^1$ is chlorine, fluorine, trifluoromethyl, methyl, nitro or amino in the 5-position, R is phenyl substituted with fluorine in the 4'-or the 2'-position, $R^2$ is methyl, hydroxyethyl or 3-hydroxypropyl, and A is as defined above, have shown especially favourable effects in the pharmacological testing, and also have few undesired side effects.

The invention moreover relates to a method for the preparation of the novel indoles of Formula I, which comprises (a) reacting an indole derivative of the following formula:

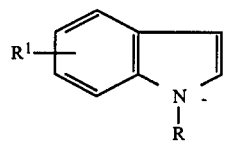

II wherein $R^1$ and R are as defined above, with a 4-piperidone of the formula:

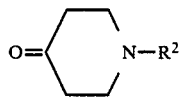

wherein $R^2$ is as defined above, or (b) reducing a compound of the following formula:

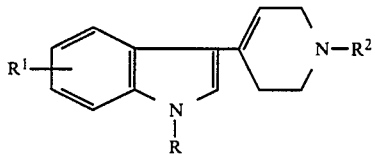

III wherein $R^1$, R and $R^2$ are as defined above, or (c) reacting a compound of the following formula:

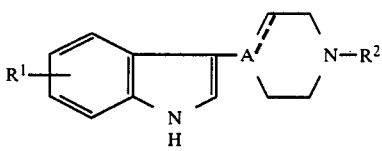

IV wherein $R^1$, $R^2$ and A are as defined above, with a compound of formula:

R-hal wherein R is as defined above and "hal" is halogen, in the presence of a metal catalyst, or (d) reacting a compound of the following formula:

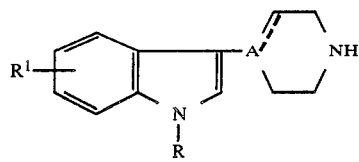

V wherein $R^1$, R and A are as defined above, with a lower alkyl halide or an epoxide of formula

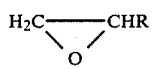

wherein R is hydrogen, methyl or ethyl, or (e) reducing a compound of the following formula:

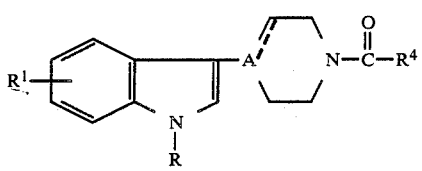

VI wherein $R^1$, R and A are as defined above and $R^4$ is hydrogen, lower alkyl (1-3 C-atoms) or lower alkoxy (1-3 C-atoms), or (f) heating a compound of the following formula:

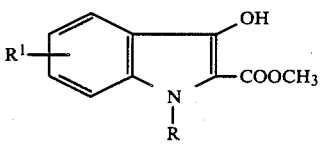

VII wherein $R^1$ and R as defined above, with a piperazine of formula: wherein $R^2$ is as defined above,

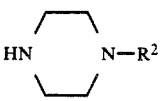

or (g) reducing a compound of the following formula:

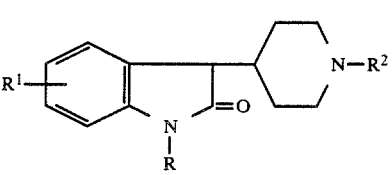

VIII wherein $R^1$, R and $R^2$ are as defined above, with a suitable reducing agent, whereupon the indole of Formula I is isolated in the form of the free base or a pharmaceutically acceptable acid addition salt thereof, and if the group $R^2$ contains one or two hydroxyl groups, if desired, acylating such a hydroxy group with a reactive derivative of an aliphatic carboxylic acid having from two to twenty-four carbon atoms, and isolating the ester formed as the free base or a pharmaceutically acceptable acid addition salt thereof.

In method (a) the reaction is performed under strong acidic conditions by heating. Trifluoroacetic acid or HCl in ethanol are preferred as acid catalysts. The starting compounds of Formula II are conveniently prepared according to procedures described in the litterature, e.g. by reduction of R substituted isatins or oxindoles by a method described by H. Sirowej et al, in Synthesis 1972, 84, according to the following reaction scheme:

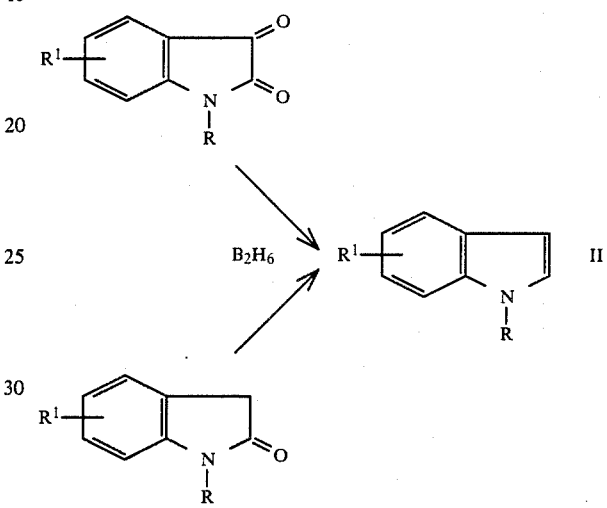

Isatins and oxindoles are prepared by a Fiedel-Craft ring closure under standard conditions from N-oxalylchloro- or N-(2-chloroacetyl) diphenylamines respectively. The compounds of Formula II may alternatively be prepared by arylation of N-unsubstituted indoles according to the method described by M.A. Khan and E.K. Rocha, Chem.Pharm.Bull. 25 (11), 3110–3114 (1977). An alternative way of obtaining the intermediates of Formula II is that from an indoxyl-2-carboxylic ester as outlined below:

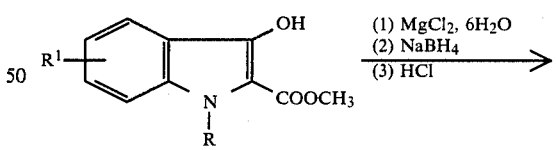

In method (b) the reduction is preferably carried out at low hydrogen pressures (3 ato.) in the presence of platinum or palladium on carbon black.

In method (c) the arylation is preferably carried out at about 160°–210° C. in aprotic polar solvents as e.g. N-methyl-2-pyrrolidone or hexamethylphosphoric triamide with $K_2CO_3$ as base and copper as a catalyst. In method (e) the reduction is preferably carried out with LiAlH4 in THF or diethylether or with diborane in THF.

Method (f) is a two step procedure in which compound VII first is decarboxyalkylated in the presence of an inorganic salt as e.g. LiCl or MgCl2 in a polar solvent as e.g. diglyme, hexamethylphosphoric triamide or N-methyl-2-pyrrolidone at elevated temperatures (120°–150° C.). Finally, the appropriate piperazine is added and the temperature raised to about 200° C. and kept there until the corresponding indoxyle has disappeared according to TLC analysis. The compounds of Formula VII are conveniently prepared according to the procedures reported by P.C. Unangst and M.E. Carethers, J.Heterocyclic Chem. 21, 709 (1984).

In method (g) diborane in THF is conveniently used as a reducing agent. The compounds of Formula VIII are prepared from the corresponding R-substituted isatins according to the following reaction scheme:

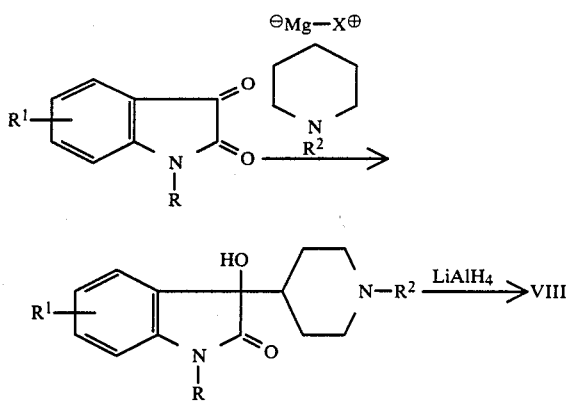

The methods of the invention shall be illustrated in the following by some examples, which may not be construed as limiting:

EXAMPLE 1

(Method a)

1-(4'-Fluorophenyl)-5-methyl-3-(1-methyl-1,2,3,6-tetrahydropyridin-4-yl)-1H-indole, hydrochloride (Lu 20-089).

1-(4'-fluorophenyl)-5-methyl-1H-indole (4.5 g) and 1-methyl-4-piperidone (5 g) were dissolved in 25 ml of acetic acid and added dropwise to 50 ml of trifluoroacetic acid kept almost at the boiling point. The mixture was gently refluxed for another ½ h. Excess trifluoroacetic acid was evaporated and the reaction mixture was added to 50 ml of 6 M HCl and 50 ml of ether. The precipitated title compound was filtered off and dried. Yield: 3.1 g (43%). M.p.262°–266° C.

In a corresponding manner the following tretrahydropyridin-4-ylindoles were prepared:
5-Fluoro-1-(4'-fluorophenyl)-3-(1-methyl-1,2,3,6-tetrahydropyridin-4-yl)-1H-indole, hydrochloride. (Lu 21-018). M.p.256° C.
1-(4'-Fluorophenyl)-3-(1-methyl-1,2,3,6-tetrahydropyridin-4-yl)-5-trifluoromethyl-1H-indole, oxalate. (Lu 21-120). M.p. 228°–229° C.
1-(4'-Fluorophenyl)-5-nitro-3-(1-methyl-1,2,3,6-tetrahydropyridin-4-yl)-1H-indole. (Lu 22-135). M.p. 168°–170° C.
1-(3'-Fluorophenyl)-5-nitro-3-(1-methyl-1,2,3,6-tetrahydropyridin-4-yl)-1H-indole, maleate. (Lu 24-004). M.p. 216°–217° C.
1-(2'-Fluorophenyl)-5-nitro-3-(1-methyl-1,2,3,6-tetrahydropyridin-4-yl)-1H-indole, maleat. (Lu 24-003). M.p. 208° C.
3-(1-(2-Hydroxyethyl)-1,2,3,6-tetrahydropyridin-4-yl)-1-(4'-trifluoromethylphenyl-1H-indole, fumarate. (Lu 24-012). M.p. 174°–175° C.
1-(4'-Fluorophenyl)-3-(1-methyl-1,2,3,6-tetrahydropyridin-4-yl)-1H-indole, hydrochloride. (Lu 23-083). M.p. 268°–270° C.
1-(4'-Fluorophenyl)-5-nitro-3-(1,2,3,6-tetrahydropyridin-4-yl)-1H-indole, maleate. (Lu 23-133). M.p. 204°–205° C.
5-Chloro-1-(4'-fluorophenyl)-3-(1-(2-hydroxyethyl)-1,2,3,6-tetrahydropyridin-4-yl)-1H-indole, hydrochloride. (Lu 23-146). M.p. 280°–282° C.
5-Chloro-1-(4'-fluorophenyl)-3-(1,2,3,6-tetrahydropridin-4-yl)-1H-indole. (Lu 23-147). M.p. 105°–107° C.
1-(4'-fluoropheynl)-3-(1-(2-hydroxyethyl)-1,2,3,6-tetrahydropyridin-4-yl)-5-nitro-1H-indole. (Lu 23-150). M.p. 151°–152° C.
1-(4'-Fluorophenyl)-3-(1,2,3,6-tetrahydropyridin-4-yl)-5-trifluoromethyl-1H-indole. (Lu 23-155). M.p. 128°–130° C.
1-(4'-Fluorophenyl)-3-(1-(2-hydroxyethyl)-1,2,3,6-tetrahydropyridin-4-yl) -5-trifluoromethyl-1H-indole. (Lu 23-156). M.p. 140°–141° C.
5-fluoro-1-(4'-fluorophenyl)-3-(1,2,3,6-tetrahydropyridin-4-yl)-1H-indole. (Lu 23-159). M.p. 75°–77° C.
5-fluoro-1-(4'-flurophenyl)-3-(1-(2-hydroxyethyl)-1,2,3,6-tetrahydropyridin-4-yl)-1H-indole, oxalate. (Lu 23-160). M.p. 180°–184° C.
5-fluoro-1-(4'-fluorophenyl)-3-(1-(2-propyl)-1,2,3,6-tetrahydropyridin-4-yl)-1H-indole, fumarate. (Lu 23-167). M.p. 190°–195° C.
1-(4'-Fluorophenyl)-3-(1-(3-hydroxypropyl)-1,2,3,6-tetrahydropyridin-4-yl) -5trifluoromethyl-1H-indole. (Lu 23-171). M.p. 159°–161° C.
5-Fluor-1-(4'-fluorophenyl)-3-(1-(3-hydroxypropyl)-1,2,3,6-tetrahydropyridin-4-yl)-1H-indole, oxalate. (Lu 23-175). M.p. 173°–175° C.

EXAMPLE 2

(method b)

1-(4'-Fluorophenyl)-3-(1-methyl-4-piperidyl)-5-trifluoromethyl-1H-indole, oxalate. (Lu 21°-131).

Compound Lu 21-120, oxalate (2.5 g) is dissloved in ethanol (200 ml), and PtO2(0.2 g) is added. Hydrogenation is continued for 3h at 3 atm. The catalyst was then filtered off, ethanol evaporated and the title compound crystallized from acetone/ether. Yield: 1.2 g (48%). M.p. 251°–252° C.

In a corresponding manner were also prepared:
1-(4'-Fluorophenyl)-3-(1-(2--imidazolidinon-1-ylethyl)-4-piperidyl)-1H-indole. (Lu 23-086). M.p. 174°–175° C.
1-(4'-Fluorophenyl)-3-(1-(1-pyrrolidin-2-onylethyl)-4-piperidyl)-5-trifluoromethyl-1H-indole, fumarate. (Lu 23-158). M.p. 240°–241° C.
5-Chloro-1-(4'-fluorophenyl)-3-(1-(2-imidazolidinon-1-ylethyl)-4-piperidyl)-1H-indole, maleate. (Lu 23-174). M.p. 155°–160° C.

EXAMPLE 3

(Method c)

3-(1-Methyl-1,2,3,6-tetrahydropyridin-4-yl)-5-nitro-1-pyridin-3-yl-1H-indole. (Lu 24-016).

3-(1-Methyl-1,2,3,6-tetrahydropyridin-4-yl)-5-nitro-
-1H-indole (4.5 g), 3-bromopyridin (6.0 g), CuBr (4.5 g)
and $K_2CO_3$ (8.0 g) were heated under stirring at 160° C.
for 2.5 h. After cooling the reaction mixture was poured
into diluted $NH_4OH$ (500 ml) and extracted with ethyl
acetate (2×300 ml). The combined organic phases were
dried ($MgSO_4$) and the solvent evaporated. The title
compound was obtained by recrystallization from acetone. Yield: 3.4 g (58%). M.p. 175°–177° C.

In a corresponding manner were also prepared:
3-(1-Methyl-1,2,3,6-tetrahydropyridin-4-yl)-5-nitro-1-pyridin-2-yl-1H-indole. (Lu24-015). M.p. 134° C.
3-(1-Methyl-1,2,3,6-tetrahydropyridin-4-yl)-5-nitro-1-(2-thiazolo-1H-indole. (Lu24-022). M.p. 204°–206° C.
5-Chloro-3-(1-methyl-1,2,3,6-tetrahydropyridin-4-yl)-1-(3-thienyl)-1H-indole, maleate. (Lu 24-001). M.p. 168°–170° C.
3-(1-Methyl-1,2,3,6-tetrahydropyridin-4-yl)-5-nitro-1-(2-thienyl)-1H-indole, maleate. (Lu 24-014). M.p. 206°–208° C.

EXAMPLE 4

(methods c and e)

5-Chloro-1-(4'-fluorophenyl)-3-(1-methyl-1,2,3,6-tetrahydropyridin-4-yl)-1H-indole, hydrobromide. (Lu 22-117).

5-Chloro-3-(1-carbethoxy-1,2,3,6-tetrahydropyridin-4-yl)-1H-indole (10 g), 1,4-fluoroiodobenzene (15 g), CuBr (10 g) and $K_2CO_3$ (15 g) in HMPA (50 ml) were heated (180°–200° C.) while stirring for 3h. After cooling the reaction mixture was poured into $H_2O$ (1 ltr.) and ethylenediamine (100 ml). The crude product was obtained by extraction twice with ether/ethyl acetate (2:1). The combined organic phases were dried ($MgSo_4$) and the solvents were evaporated. The pure 5-chloro-1-(4'-fluorophenyl)-3-(1-carbethoxy-1,2,3,6-tetrahydropyridin-4-yl)-1H-indole was obtained by column chromatography on silica gel (eluent 30% ether in dichloromethane). Yield: 8.9 g (68%). M.p. 120°–122° C. The carbethoxy compound then obtained (3 g) was dissolved in dry THF (50 ml) and $LiAlH_4$ pellets (2 g) were added. The mixture was refluxed for 1h, cooled and $H_2O$/THF added to destroy excess $LiAlH_4$. The precipitate was filtered off and THF evaporated. The remaining oil was dissolved in acetone and the title compound precipitated as a hydrobromide salt. Yield: 2.4 g (75%). M.p. 258° C.

In a corresponding manner were also prepared:
5-Chloro-1-(4'-fluorophenyl)-3-(1-isobutyl-1,2,3,6-tetrahydropyridin-4-yl)-1H-indole, hydrobromide. (Lu 22-134). M.p. 285°–286° C.
5-Fluro-3-(1-methyl-1,2,3,6-tetrahydropyridin-4-yl)-1-(2-thiazolo)-1H-indole, fumarate. (Lu 24-013). M.p. 190°–194° C.

EXAMPLE 5

(method d)

5-Fluoro-2-(4'-fluorophenyl)-3-(1-(2-imidazolidinon-1-ylethyl)-1,2,3,6-tetrahydropyridin-4-yl)-1H-indole, oxalate. (Lu 21-046)

5-Fluoro-1-(4'-fluorophenyl)-3-(1,2,3,6-tetrahydropyridin-4-yl)-1H-indole (2g) prepared as described in Example 1; 1-chloroethyl-2-imidazolidinon (2 g), $K_2CO_3$ (3 g) and a small crystal of KI were refluxed in methyl isobytyl ketone (50 ml) for 16 h. The reaction mixture was poured into $H_2O$ and $CH_2Cl_2$ (200 ml) was added. The organic phase was separated, dried ($MgSO_4$) and the solvents evaporated. The crude product was dissolved in acetone and precipitated as an oxalate salt. Yield: 1.2 g (36%). M.p. 186°–189° C.

In a corresponding manner the following indoles were prepared:
1-(4'-Flurophenyl)-3-(4-(2-imidazolidinon-1-ylethyl)-1-piperazino)-5-trifluoromethyl-1H-indole, dihydrobromide. (Lu 23-001). M.p. 262°–263° C.
1-(4'-Fluorophenyl)-3-(4-(1-pyrrolidin-2-onylethyl)-1-piperazino)-5-trifluoromethyl-1H-indole. (Lu 22-133). M.p. 224°–227° C.
1-(4'-Fluorophenyl)-5-nitro-3-(1-pyrrolidin-2-onylethyl)-1,2,3,6-tetrahydropyridin-4-yl)-1H-indole, hydrochloride (Lu 23-024). M.p. 263°–265° C.
1-(4'-Fluorophenyl)-3-(1-(2-imidazolidinon-1-ylethyl)-1,2,3,6-tetrahydropyridin-4-yl)-1H-indole, hydrochloride. (Lu 23-075). M.p. 259°–262° C.
1-(4'-Fluorophenyl)-5-nitro-3-(1-(2-oxazolidinon-3-ylethyl)-1,2,36-tetrahydropyridin-4-yl)-1H-indole, maleate (Lu 23-134). M.p. 128°–130° C.
1-(4'-Fluorophenyl)-3-(1-(2-imidazolidinon-1-ylethyl)-1,2,3,6-tetrahydropyridin-4-yl)-5-nitro-1H-indole. (Lu 23-142). M.p. 177°–179° C.
5-Chloro-1-(4'-fluorophenyl)-3-(1-(2-imidazolidinon-1-ylethyl)-1,2,3,6-tetrahydropyridin-4-yl)-1H-indole. (Lu 23-148). M.p. 138°–140° C.
1-(4'-Fluorophenyl)-3-(1-(2-imidazolidinon-1-ylethyl)-1,2,3,6-tetrahydropridin-4-yl)-5-trifluoromethyl-1H-indole. (Lu 23-157). M.p. 164°–165° C.
1-(2'-Fluorophenyl)-3-(1-(2-imidazolidinon-1-ylethyl)-1,2,3,6-tetrahydropridin-4-yl)-5-nitro-1H-indole, maleate. (Lu 24-024). M.p. 200° C.

EXAMPLE 6

(Method e)

1-(4'-Fluorophenyl)-3-(1-pyrrolo-2-ethyl)-1,2,3,6-tetrahydropyridin-4-yl)-5-trifluoromethyl-1H-indole. maleate. (Lu 23-172).

1-(4'-Fluorophenyl)-3-(1-pyrrolo-2-aceto)-1,2,3,6-tetrahydropyridin-4-yl)-5-trifluoromethyl-1H-indole (2.5g) was refluxed with $LiAlH_4$(1g)indry THF (50ml) for 1.5h. After cooling $H_2O$/THF was added to destroy excess of $LiAlH_4$. The precipitate was filtered off and THF evaporated. The remaining oil was dissolved in 2-propanol and the title compound precipitated as a maleate. Yield: 1.3 g (42%). M.p. 194°–195° C.

In a corresponding manner were also prepared:
1-(4'-Fluorophenyl)-3-(1-(2-methyl-1-imidazole-2-ethyl)-1,2,3,6-tetrahydropyridin-4-yl)-5-trifluoromethyl-1H-indole, difumarate. (Lu 23-173). M.p. 189°–191° C.
1-(4'-Fluorophenyl)-3-(1-(1-imidazole-2-ethyl)-1,2,3,6-tetrahydropyridin-4-yl)-5-trifluoromethyl-1H-indole, dimaleate. (Lu 24-002). M.p. 165°–167° C.

EXAMPLE 7

(method f)

1-(4'-Fluorophenyl)-3-(4-methylpiperazio)-5-trifluoromethyl-1H-indole, dihydrochloride. (Lu 21-123).

2-Carboxymethyl-1-(4'-fluorophenyl)-5-trifluoromethylindolin-3-on (15 g) and $MgCl_2·6H_2O$ (30 g) in HMPA (100 ml) were heated under $N_2$ at 120°–140° C. for 1 h and finally at 150° C. for another ½ h. 1-Methylpiperazin (25 ml) was added and the mixture was refluxed under $N_2$ at an oil bath temperature of 200° C. for 16 h. The mixture was cooled and poured into 1 ltr. of H₂O and extracted with ether (3×200 ml). The combined ether extracts were washed with 0.5 M HCl (3×300 ml). The acidic H₂O phase was made alkaline and reextracted with ether (2×200 ml). The combined organic phase was dried (MgSO₄) and the ether evaporated. The remaining oil was dissolved in acetone and the title compound precipitated as a dihydrochloride. Yield: 6.7 g (35%). M.p. 245°–247° C.

In a corresponding manner the following 3-piperazinoindoles were prepared:

1-(4'-Flurophenyl)-3-(4-(2-hydroxyethyl)-piperazino)-5-trifluoromethyl-1H-indole. (Lu 21-152). M.p. 164° C.

1-(4'-Fluorophenyl)-3-piperazino-5-trifluoromethyl-1H-indole. (Lu 21-153). M.p. 168°–170° C.

1-(4'-Fluorophenyl)-3-(4-isopropyl-piperazino)-5-trifluoromethyl-1H-indole, dihydrochloride. (Lu 23-016). M.p. 278°–280° C.

5-Chloro-3-(4-methylpiperazino)-1-phenyl-1H-indole. (Lu 23-015). M.p. 174°–175° C.

EXAMPLE 8

(method g)

1-(4'-Fluorophenyl)-5-methyl-3-(1-methyl-4-piperidyl)-1H-indole, hydrobromide. (Lu 21-037).

To 14 g of Mg turnings was added 4-chloro-1-methyl-piperidine (35 g) in dry THF (500 ml). The mixture was refluxed for 1 hour and filtered under N₂ into an ice cooled solution of 1-(4'-fluorophenyl)-5-methylisatin (60 g) in dry THF (500 ml). The mixture was heated to reflux and poured into H₂O (1 ltr.) saturated with NH₄Cl and extracted with ether (2×300 ml). The combined organic phases were dried (MgSO₄), the ether evaporated yilding 48.5 g (58%) of 1-(4'-fluorophenyl-3-hydroxy-5-methyl-3-(1-methyl-4-piperidyl)indolin-2-on. M.p. 177°–179° C. // To a suspension of LiAlH₄ (1 g) in dry THF (100 ml) was added 2.5 g of the above prepared indolin-2-on. The mixture was refluxed for 1 hour, excess of LiAlH₄ destroyed by addition of H₂O / THF, and filtered; and 2 M HCl (500 ml) was added to the filtrate and gently heated. The H₂O phase was made alkaline and the product extracted with ether (2×300 ml). The combined ether phases were dried (MgSO₄) and the ether evaporated. The remaining oil was dissolved in acetone and 1-(4'-fluorophenyl)-5-methyl-3-(1-methyl-4-piperidyl)indolin-2-on was precipitated as an oxalate. Yield: 2.0 g (66%). M.p. 222° C. To a solution of B₂H₆ in THF (100 ml) kept under N₂ at 0° C. was added 11.0 g of the oxalate salt prepared as above. The mixture was heated slowly to 50° C. and kept there for 2 hours. It was finally poured onto ice (1 ltr.) and extracted with ether (2×200 ml). The combined ether phases were dried (MgSO₄) and the ether evaporated. The remaining oil was dissolved in 2-propanol and the title compound precipitated as a hydrobromide salt. Yield: 3.7 g (36%). M.p. 254°–256° C.

EXAMPLE 9

5-Amino-1-(4'-fluorophenyl)-3-(1-methyl-1,2,3,6-tetrahydropyridin-4-yl)-1H-indole, fumarate. (Lu 23-149)

1-(4'-Fluorophenyl)-3-(methyl-1,2,3,6-tetrahydropyridin-4-yl)-5-nitro-1H-indole (Lu 22-135) (10 g) in 90% ethanol (150 ml) was heated to reflux and dil. HCl (2 ml) and Fe-powder (5 g) were added within 0.5 hour. Reflux was continued for another hour. The reaction mixture was filtered, cooled down and subsequently poured into 1 liter of NH₄Oh and extracted with ethyl acetate (2×400 ml). The combined organic phases were dried (MgSO₄) and the solvent evaporated. The remaining oil and purified by column chromatography on silica gel (eluted with ethyl acetate/methanol 1:1 containing 2% of triethylamine). The title compound was finally precipitated as a fumarate from ethanol/acetone (1:1). Yield 4.2 g (34%). M.p. 128°–134° C.

EXAMPLE 10

1-(4'-Fluorophenyl)-3-(4-(2-(pyrrolidin-2-thion-1-yl)-ethyl)-1-piperazino)-5-trifluoromethyl-1H-indole (Lu23-018).

The pyrrolidonyl indole derivative (Lu 22-133) (2.8 g) prepared in Example 4 and p-methoxyphenylthionophosphine sulfide dimer (2.0 g) (Lawesson reagent) were heated in HMPA (25 ml) at 110° C. for 1 hour. The reaction mixture was poured into H₂O (500 ml) and K₂CO₃ (10 g) added. The product was extracted with ether containing 10% of ethyl acetate (2×200 ml). The combined organic phases were dried (MgSO₄), the solvents evaporated and the resulting crystalline product was recrystallized from ethanol yielding 2.1 g (73%) of the title compound. M.p. 199°–201° C.

EXAMPLE 11

3-(4-(1-Acetyloxyethyl)-1-piperazino)-1-(4'-fluorophenyl)-5-trifluoromethyl-1H-indole. (Lu 23-161).

1-(4'Fluorophenyl)-3-(4-(2-hydroxyethyl)-1-piperazino)-5-trifluoromethyl-1H-indole (Lu 21-152) (5 g) was heated to reflux in acetone (50 ml). Acetylchloride (2 ml) was added slowly. Refluxing was continued for 1.5 h. The solvent was evaporated and the remaining oil was extracted with CH₂Cl₂ (2×200 ml) from NH₄OH at Ph 10. The combined organic phases were dried (MgSO₄) and the solvent evaporated. The title compound precipitated from ether. Yield: 3.7 g (72%). M.p. 129°–131° C.

In a corresponding manner the following esterified indole derivatives were prepared:

3-(4-(1-decanoyloxyethyl)-1-piperazino)-1-(4'-fluorophenyl)-5-trifluoromethyl-1H-indole. (Lu 23-162). M.p. 71°–73° C.

1-(4'-Fluorophenyl)-3-(4-(1-oleyloxyethyl)-1-piperazino)-5-trifluoromethyl-1H-indole, dihydrochloride. (Lu 23-163). M.p. 158°–162° C.

The compounds of Formula I were tested according to reliable and well recognized pharmacological tests as follows:

1. Methylphenidate antagonism

The inhibiting effect of test substances on the methylphenidate-induced gnawing in mice is determined as described by Pedersen and Christensen (1972). The test substance is given i.p. in different doses, while methylphenidate is given s.c. in the dose 60 mg/kg, ½, 2 or 24 hours after injection of test substance. Per dose of the test substance is used 3×2 mice (8, 18–25 g). The results are given in fractions: 0/3, ⅓, ⅔ and 3/3, where 0,1,2 and 3 are the number of pairs, which has not been gnawing on receipt of the test substance.

Ref:

Pedersen, V. and Christensen, A.V.: Acta pharmacol. et toxicol. 31, 488–496, 1972.

2. Catalepsy

Evaluation of catalepsy is made according to Arnt (1983). The rat is placed on a vertical wire mesh (mesh diameter 12 mm) and considered as cataleptic if it remains immobile for more than 15 seconds. The number of cataleptic rats in each dose group is determined every hour, 1–6 hours and 24 hours following peroral administration of test compound. The maximal numbers of cataleptic rats in each of at least 3 dose groups, each consisting of at least 4 rats, is recorded. These numbers are used for calculation of $ED_{50}$ values by log-probit analysis.

Ref.:
Arnt, J.: European J. Pharmacol. 90, 47–55, 1983.

3. Quipazine inhibition

Quipazine and a number of other compounds, which increase 5-$HT_2$ receptor activity in the CNS, induce a characteristic rapid shake (twitch) of the head. This response is inhibited by 5-$HT_2$ receptor antagonists (Vetulani et al. 1980, Arnt et al. 1984).

The test compound or saline is injected subcutaneously 2 hours before subcutaneous injection of quipazine hemimalecate (15umol/kg). At least 3 dose groups, each consisting of at least 4 rats, are used. The rats are individually placed in observation cages (12×25 cm) and the number of head twitches are counted 30–40 min after quipazine administration. Inhibition of head twitches is expressed in per cent of the number of head twitches in the control group. ED 50 values are calculated by log-probit analysis.

Ref.:
Vetulani, J., B.B. Beduarczyk, K. Reichenberg and A. Rokost: Neuropharmacology 19, 155–158, 1983.
Arnt, J., J. Hyttel and J.-J. Larsen: Acta pharmacol. et toxicol. 55, 363–372, 1984.

4. $^3$H-spiroperidol bindings

The affinity of compounds to dopamine (DA) D-2 receptors and serotomin$_2$(5-$HT_2$) receptors was determined by in vitro receptor binding technique. Binding of $^3$H-spiroperidol to DA D-2 receptors in rat striatal membranes and to 5-$HT_2$ receptors in rat cortical membranes was determined as described in detail by Arnt et al. (1984).

Ref.:
Arnt, J., J. Hyttel and J.-J. Larsen: Acta pharmacol. et toxicol. 55, 363–372, 1984.

TABLE 1

| | Pharmacology of Indoles | | | | $^3$H-Spiroperidol bindings | |
|---|---|---|---|---|---|---|
| | MePh | Catalep. | | Qvipaz. | DA-2 | 5-$HT_2$ |
| | Antg. | ED50(po) | | inh. | receptors | |
| Compound | ED50(ip) | (μmol/kg) | | ED50(sc) | | |
| No. | (μmol/kg) | 1–6 h | 24 h | (μmol/kg) | $IC_{50}/10^{-9}$ M | |
| Lu 20-089 | 0.18 | 0.43 | 6.5 | 0.12 | 0.34 | 1.8 |
| Lu 21-018 | 0.58 | 2.00 | >6.9 | 0.15 | 0.74 | 3.0 |
| Lu 21-037 | 2.10 | | | | | |
| Lu 21-046 | 48.1 | | | 0.23 | | |
| Lu 21-120 | 0.08 | 0.32 | 0.35 | 0.03 | 0.61 | 3.1 |
| Lu 21-123 | 0.09 | 0.08 | 0.62 | 0.035 | 1.7 | 6.7 |
| Lu 21-131 | 0.60 | 0.59 | 2.2 | | | |
| Lu 21-152 | 0.11 | 0.17 | 0.28 | 0.023 | 2.8 | 7.4 |
| Lu 21-153 | 2.0 | 7.1 | 16.0 | 0.37 | 3.7 | 6.7 |
| Lu 22-117 | 0.06 | 0.09* | >0.37* | 0.052 | 1.2 | 0.66 |
| Lu 22-133 | 0.82 | 0.66* | 1.7* | 0.15 | | 1.9 |
| Lu 22-134 | 1.7 | 2.7* | >2.7* | 2.5 | 5.3 | |
| Lu 22-135 | 0.10 | 0.078 | >0.89* | 0.009 | 1.1 | 1.9 |
| Lu 23-001 | 0.22 | 1.2 | 2.6 | 0.047 | 6.6 | 18 |
| Lu 23-011 | 0.12* | 0.55 | >1.8 | 0.041 | | 0.38 |
| Lu 23-015 | 8.8 | 12.0 | >15 | 0.062 | 12.0 | 3.9 |
| Lu 23-018 | 53.0 | 1.2 | 2.9 | | | |
| Lu 23-024 | 0.65 | 6.8* | >10* | | | 5.3 |
| Lu 23-075 | 19* | | | 0.18 | | |
| Lu 23-083 | 1.3* | 9.4 | >14 | 0.15 | 1.8 | |
| Lu 23-086 | >98* | | | 0.036 | 42 | 2.9 |
| Lu 23-133 | 18* | 11.0 | >11 | | 5.9 | |
| Lu 23-134 | 9.0* | 1.1 | >8.8 | | 2.8 | 15 |
| Lu 23-142 | 2.6* | | | | | 6.7 |
| Lu 23-143 | 72.0* | >18* | >18* | 4.5 | | |
| Lu 23-146 | 0.73* | 1.0* | | | | |
| Lu 23-147 | >99* | | | | | |
| Lu 23-148 | >91* | | | | | |
| Lu 23-149 | 0.45* | | | | | |
| Lu 23-150 | 0.07* | 0.21 | | | 4.7 | 10 |
| Lu 23-155 | 3.8* | | | | | |
| Lu 23-156 | 0.07* | <0.19* | 1.1* | 0.03 | 19 | 15 |
| Lu 23-157 | 0.37* | 0.49* | 2.6* | 0.12 | | |
| Lu 23-158 | 2.9* | | | 0.11 | | |
| Lu 23-159 | 47* | | | | | |
| Lu 23-160 | 3.4* | | 5.2* | | 11 | 34 |
| Lu 23-161 | 0.05* | 0.09* | 0.18* | | | |
| Lu 23-162 | 1.7* | | | | | |
| Lu 23-163 | 1.1* | | | | | |
| Lu 23-167 | 2.7* | 2.7* | >11.0* | | | |
| Lu 23-171 | 0.11* | | | | | |
| Lu 23-172 | >70* | | | >0.55 | 31 | |
| Lu 23-173 | 0.77* | 1.8* | | >7.1 | 42 | 60 |
| Lu 23-174 | >72* | | | 0.49 | 20 | 6.6 |
| Lu 23-175 | 0.32* | 0.68* | | | 11 | 6.7 |
| Lu 24-001 | 2.6 | | | 0.19 | | 8.8 |
| Lu 24-002 | 0.45* | | | >0.45 | | |
| Lu 24-003 | 0.09* | | | | 6.0 | 14 |
| Lu 24-004 | 1.1* | | | | | |
| Lu 24-012 | >20* | | | | | |

TABLE 1-continued

| Compound No. | MePh Antg. ED50(ip) (μmol/kg) | Catalep. ED50(po) (μmol/kg) 1-6 h | Catalep. ED50(po) (μmol/kg) 24 h | Qvipaz. inh. ED50(sc) (μmol/kg) | $^3$H-Spiroperidol bindings DA-2 receptors IC$_{50}$/10$^{-9}$ M | $^3$H-Spiroperidol bindings 5-HT$_2$ receptors IC$_{50}$/10$^{-9}$ M |
|---|---|---|---|---|---|---|
| Pharmacology of Indoles | | | | | | |
| Lu 24-013 | >20* | | | | | |
| Lu 24-014 | >22* | | | | | |
| Lu 24-015 | 3.8* | | | | | |
| Lu 24-016 | >30* | | | | | |
| Lu 24-022 | | | | | | |
| Lu 24-024 | | | | | | |
| Clorpromazine | 23 | 70 | | 0.38 | 24 | 30 |
| Cis(Z)Flupentixol | 0.14 | 2.4 | 19 | 0.042 | 3.2 | 13 |
| Haloperidol | 0.11 | 1.0 | | 0.99 | 8.2 | 58 |
| Tefludazine | 0.06 | 0.61 | 0.9 | 0.06 | 19 | 8.6 |

*ED50 from sc administration

LD$_{50}$ i.v. mice was determined for Lu 21-152 and Lu 22-135 to be 147 μmol/kg and 276 μmol/kg respectively which indicates a comparatively low acute toxicity as compared with known neuroleptics such as chlorpromazine, cis(Z)-flupentixol and tefludazin having values between 120–180 μmol/kg.

The compounds of Formula I and the non-toxic acid addition salts thereof may be administered to animals such as dogs, cats, horses, sheeps or the like, including human beings, both orally and parenterally, and may be used for example in the form of tablets, capsules, powders, syrups or in the form of the usual sterile solutions for injection. - Results upon administration to human beings have been very gratifying.

Most conveniently the compounds of Formula I are administered orally in unit dosage form such as tablets or capsules, each dosage unit containing the free amine or a non-toxic acid addition salt of one of the said compounds in a amount of from about 0.10 to about 100 mg, most preferably, however, from about 5 to 50 mg, calculated as the free amine, the total daily dosage usually ranging from about 1.0 to about 500 mg. The exact individual dosages as well as daily dosages in a particular case will, of course, be determined according to established medical principles under the direction of a physician.

When preparing tablets, the active ingredient is for the most part mixed with ordinary tablet adjuvants such as corn starch, potato starch, talcum, magnesium stearate, gelatine, lactose, gums, or the like.

When the compound of Formula I is an ester, preferably a decanoic acid ester, palmitic acid ester or a behenic acid ester, the composition may advantageously be an oily solution for injection, and such solutions often have a very prolonged effect when compared with the corresponding unesterified compound.

Typical examples of formulas for composition containing 1-(4'fluorophenyl)-3-(4-(2-hydroxyethyl-1-piperazinyl)-5-trifluoromethylindole (called Lu 21-152 for short) as the active ingredient, are as follows:

(1) Tablets containing 5 milligrams of Lu 21-152 calculated as the free base:

| Lu 21-152 | 5 mg |
| Lactose | 18 mg |
| Potato starch | 27 mg |
| Saccharose | 58 mg |
| Sorbitol | 3 mg |
| Talcum | 5 mg |
| Gelatine | 2 mg |
| Povidone | 1 mg |
| Magnesium stearate | 0.5 mg |

(2) Tablets containing 50 milligrams of Lu 21-152 calculated as the free base:

| Lu 21-152 | 50 mg |
| Lactose | 16 mg |
| Potato starch | 45 mg |
| Saccharose | 106 mg |
| Sorbitol | 6 mg |
| Talcum | 9 mg |
| Gelatine | 4 mg |
| Povidone | 3 mg |
| Magnesium stearate | 0.6 mg |

(3) Syrup containing per milliliter:

| Lu 21-152 | 10 mg |
| Sorbitol | 500 mg |
| Tragacanth | 7 mg |
| Glycerol | 50 mg |
| Methyl-paraben | 1 mg |
| Propyl-paraben | 0.1 mg |
| Ethanol | 0.005 ml |
| Water | ad 1 ml |

(4) Solution for injection containing per milliliter:

| Lu 21-152 | 50 mg |
| Acetic acid | 17.9 mg |
| Sterile water | ad 1 ml |

(5) Solution for injection containing per milliliter:

| Lu 21-152 | 10 mg |
| Sorbitol | 42.9 mg |
| Acetic acid | 0.63 mg |
| Sodium hydroxide | 22 mg |
| Sterile water | ad 1 ml |

Any other pharmaceutical tableting adjuvants may be used provided that they are compatible with the active ingredient, and additional compositions and dosage forms may be similar to those presently used for neuroleptics, such as chlorpenthixol, flupentixol or fluphenazine.

Also combinations of the compounds of Formula I as well as their non-toxic acid salts with other active ingredients, especially other neuroleptics, thymoleptics, tranquilizers, analgetics or the like, fall within the scope of the present invention.

As previously stated, when isolating the compounds of Formula I in the form of an acid addition salt the acid is preferably selected so as to contain an anion which is non-toxic and pharmacologically acceptable, at least in usual therapeutic doses. Representative salts which are included in this preferred group are the hydrochlorides, hydrobromides, sulphates, acetates, phosphates, nitrates, methanesulphonates, ethane-sulphonates, lactates, citrates, tartrates or bitartrates, pamoates and maleates of the amines of Formula I. Other acids are likewise suitable and may be employed if desired. For example: fumaric banzoic, ascorbic, succinic, salicylic, bismethylenesalicylic, propionic gluconic, malic, malonic, mandelic, cannamic, citraconic, stearic, palmitic, itaconic, glycolic, benzenesulphonic, and sulphamic acids may also be employed as acid addition saltforming acids.

When it is desired to isolate a compound of the invention in the form of the free base, this may be done according to conventional procedure as by dissolving the isolated or unisolated salt in water, treating with a suitable alkaline material, extracting the liberated free base with a suitable organic solvent drying the extract and evaporating to dryness or fractionally distilling to effect isolation of the free basic amine.

The invention also comprises a method for the alleviation, palliation, mitigation or inhibition of the manifestations of certain physiological-psychological abnormalies of animals, including psychoses, by administering to a living animal body, including human beings, an adequate quantity of a compound of Formula I or a non-toxic acid addition salt thereof. An adequate quantity would be from about 0.001 mg to about 10 mg per kg of body weight in each unit dosage, and from about 0.003 milligrams to about 7 milligrams/kg of body weight per day.

It is to be understood that the invention is not limited to the exact details of operation or exact compound or compositions shown and described, as obvious modifications and equivalents will be apparent to one skilled in the art.

I claim:

1. A compound selected from the group consisting of a) an indole derivative of the following formula:

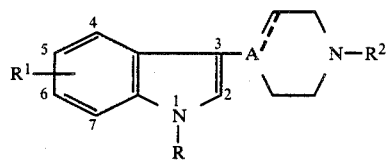

wherein R is selected from phenyl, optionally substituted with one substituent selected from halogen and trifluoromethyl and a hetero aromatic group selected from 2-thienyl, 3-thienyl, 2-furoyl, 3-furoyl, 2-thiazol, 2-oxazol, 2-imidazole, 2-pyridyl, 3-pyridy and 4-pyridyl;

$R^1$ is selected from hydrogen, halogen, lower alkyl, lower alkoxy, hydroxy, cyano, nitro, lower alkylthio, trifluoromethyl, lower alkylsulfonyl, amino, lower alkylamino and lower di-alkylamino;

"A" is selected from nitrogen and carbon, and the dotted line indicates - when A is carbon - an optional bond;

$R^2$ is selected from hydrogen, cycloakyl of $C_3$-$C_4$ inclusive lower alkyl and lower alkenyl, optionally substituted with one or two hydroxy groups, any hydroxy group present being optionally esterified with an aliphatic carboxylic acid having from two to twenty-four carbon atoms inclusive, and the group

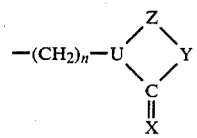

wherein "n" is an integer of 2-6;

X is selected from oxygen and sulfur, C=X may constitute the group CH= when Y is selected from =N— and =CH—;

Y is selected from oxygen, sulfur, $CH_2$ and N-$R^3$, where $R^3$ is selected from hydrogen and lower alkyl, lower alkenyl and a cycloalkylmethyl group, said "cycloalkyl" having from three to six carbon atoms inclusive;

Z is selected from —$(CH_2)_m$—, "m" being selected from 2 and 3, and -CH=CH and 1,2-phenylene optionally substituted with a group selected from halogen and trifluoromethyl, and —CO (or S)$CH_2$—;

U is selected from nitrogen and carbon, provided that when $R^1$ is chloro, A is nitrogen and $R^2$ is selected from methyl and cyclohexyl, R may not be phenyl; and (b) a pharmaceutically acceptable acid addition salt thereof.

2. An indole derivative of claim 1, wherein $R^1$ is selected from chlorine, fluorine, trifluoromethyl, methyl, nitro and amino in the 5-position, R is phenyl substituted with fluorine in the 4'- or 2'-position, $R^2$ is selected from methyl, 2-hydroxyethyl and 3-hydroxypropyl, and A is as defined in claim 1.

3. Claim 1 compound selected from 1-(4'-Fluorophenyl)-3-(4-(2-hydroxyethyl)-piperazino)-5-trifluoromethyl-1H-indole, 1-(4'-Fluorophenyl)-5-nitro-3-(1-methyl-1,2,3,6-tetrahydropyridin-4-yl)-1H-indole, 5-Chloro-1-(4'-fluorophenyl)-3-(1-methyl-1,2,3,6-tetrahydropyridin-4-yl)-1H-indole, 1-(4'-Fluorophenyl)-3-(1-(2-hydroxyethyl)-1,2,3,6-tetrahydropyridin-4-yl)-5-nitro-1H-indole, 1-(4'-Fluorophenyl)-3-(1-(2-hydroxyethyl)-1,2,3,6-tetrahydropyridin-4-yl)-5-trifluoromethyl-1H-indole, 5-Fluoro-1-(4'-fluorophenyl)-3-(1-(3-hydroxypropyl)-1,2,3,6-tetrahydropyridin-4-yl)-1H-indole, and pharmaceutically acceptable acid addition salts thereof.

4. A neuroleptic or thymoleptic pharmaceutical composition suitable for use in the treatment of disorders amenable to such medication in unit dosage form comprising, as active ingredient, a compound as defined in claim 1 in an amount effective for such purpose, together with one or more pharmaceutical diluents or carriers.

5. A pharmaceutical composition in unit dosage form, according to claim 4, wherein the active ingredient is present in an amount from 0.10 to 100 milligrams per unit dosage.

6. A pharmaceutical composition in unit dosage form, according to claim 4 wherein the active ingredient is a compound of claim 3.

7. A method for the treatment of disorders comprising administering amount in unit dosage form of a compound of claim 1, as an active ingredient, optionally together with one or more pharmaceutical diluents or carriers, to a warmblooded animal including a human being.

8. A method according to claim 7, wherein the active ingredient is present in an amount from 0.1 to about 100 mg per unit dosage.

9. A method according to claim 8, wherein the active ingredient is 1-(4'-fluorophenyl)-3-(4-(2-hydroxyethyl-1-piperazinyl)-5-trifluoromethyl-indole, or a pharmaceutically acceptable salt thereof.

* * * * *

UNITED STATES PATENT AND TRADEMARK OFFICE
CERTIFICATE OF CORRECTION

PATENT NO. : 4,710,500

DATED : December 1, 1987

INVENTOR(S) : Jens K. Perregaard

Page 1 of 2

It is certified that error appears in the above-identified patent and that said Letters Patent is hereby corrected as shown below:

Col. 1, line 35; "wellknown" should read -- well-known --
Col. 1, line 62; "immiscbile" should read -- immiscible --
Col. 2, line 9; "wellknown" should read -- well-known --
Col. 3, line 45; delete "wherein $R^2$ is as defined above,"
Col. 3, line 51; just below the formula and on the blank line above "or" insert the following; -- wherein $R^2$ is as defined above, --
Col. 4, lines 9 & 10; "litterature," should read -- literature, --
Col. 4, line 43; start a new paragraph with "An alternative"
Col. 6, line 2; "maleat." should read -- maleate. --
Col. 6, line 16; "-tetrahydropri-" should read -- -tetrahydropyri- --
Col. 6, line 18; "1-(4'-fluoropheynl)-" should read -- 1-(4'-fluorophenyl)- --
Col. 6, line 39; "5-Fluor-" should read -- 5-Fluoro- --
Col. 6, line 46; "(Lu 21°-" should read -- (Lu 21- --
Col. 7, line 64; "Kl" should read -- KI --
Col. 8, line 21, 27 and 30; in all three instances change "-tetrahydropridin-" to read -- -tetrahydropyridin- --
Col. 8. line 41; "LiAlH$_4$(1g)indry" should read -- LiAlH$_4$ (1g) in dry --
Col. 8, line 59; "-(4-methylpiperazio)-" should read -- -(4-methylpiperazino)- --
Col. 9, line 11; "1-(4'-Flurophenyl)-" should read -- 1-(4'-Fluorophenyl)- --
Col. 9, line 34; "yilding" should read -- yielding --
Col. 10, line 53; start a new paragraph with "The test"
Col. 10, line 57; "(8," should read -- ( ♂, --
Col. 11, line 18; "hemimalecate (15 umol/kg)." should read -- hemimaleate (15 μmol/kg). --
Col. 13, line 18; "i.v. mice" should read -- i.v. in mice --
Col. 13, line 36; "a" should read -- an --
Col. 14, line 68; "banzoic," should read -- benzoic, --

UNITED STATES PATENT AND TRADEMARK OFFICE
CERTIFICATE OF CORRECTION

PATENT NO. : 4,710,500
DATED : December 1, 1987
INVENTOR(S) : Jens K. Perregaard It is certified that error appears in the above—identified patent and that said Letters Patent is hereby corrected as shown below:

Col. 15, line 1; insert a comma -- , -- after "propionic"
Col. 15, lines 16 & 17; "abnormalies" should read -- abnormalities --
Col. 15, line 46; "3-pyridy" should read -- 3-pyridyl --
Col. 15, line 55; "$C_3 - C_4$" should read -- $C_3 - C_6$ --
Col. 15, line 56; insert a comma -- , -- after "inclusive"
Col. 16, line 16; "Ais" should read -- A is --
Col. 16, line 55; after "disorders" insert -- amenable to neuroleptic or thymoleptic medication --
Col. 16, line 56; after "administering" insert -- a neuroleptically- or thymoleptically-effective --.

Signed and Sealed this

Second Day of August, 1988

Attest:

DONALD J. QUIGG

Attesting Officer

Commissioner of Patents and Trademarks